United States Patent [19]

Klawitter

[11] 4,443,894
[45] Apr. 24, 1984

[54] HEART VALVE WITH DOG-LEG PIVOT

[75] Inventor: Jerome J. Klawitter, Austin, Tex.

[73] Assignee: Hemex, Inc., Austin, Tex.

[21] Appl. No.: 367,298

[22] Filed: Apr. 12, 1982

[51] Int. Cl.³ .............................................. A61F 1/22
[52] U.S. Cl. .................................... 3/1.5; 137/512.1;
137/527; 137/527.8
[58] Field of Search .................. 3/1.5; 137/512.1, 527, 137/527.8

[56] References Cited

U.S. PATENT DOCUMENTS

| 4,011,601 | 3/1977 | Clune et al. | 3/1.5 |
| 4,159,543 | 7/1979 | Carpentier | 3/1.5 |
| 4,178,639 | 12/1979 | Bokros | 3/1.5 |
| 4,254,508 | 3/1981 | Bokros | 3/1.5 |
| 4,363,142 | 12/1982 | Meyer | 3/1.5 |

*Primary Examiner*—Ronald L. Frinks
*Attorney, Agent, or Firm*—Fitch, Even, Tabin & Flannery

[57] ABSTRACT

A heart valve having a pair of leaflets which are guided between their open and closed positions by guides extending outward and received in dog-leg shaped depressions. The depressions each have a downstream section, which angles outward from a centerline plane of the valve body and a connected vertical upstream section. In the closed position the guides reside in intermediate locations to unload the force between the guides and the depression walls.

21 Claims, 9 Drawing Figures

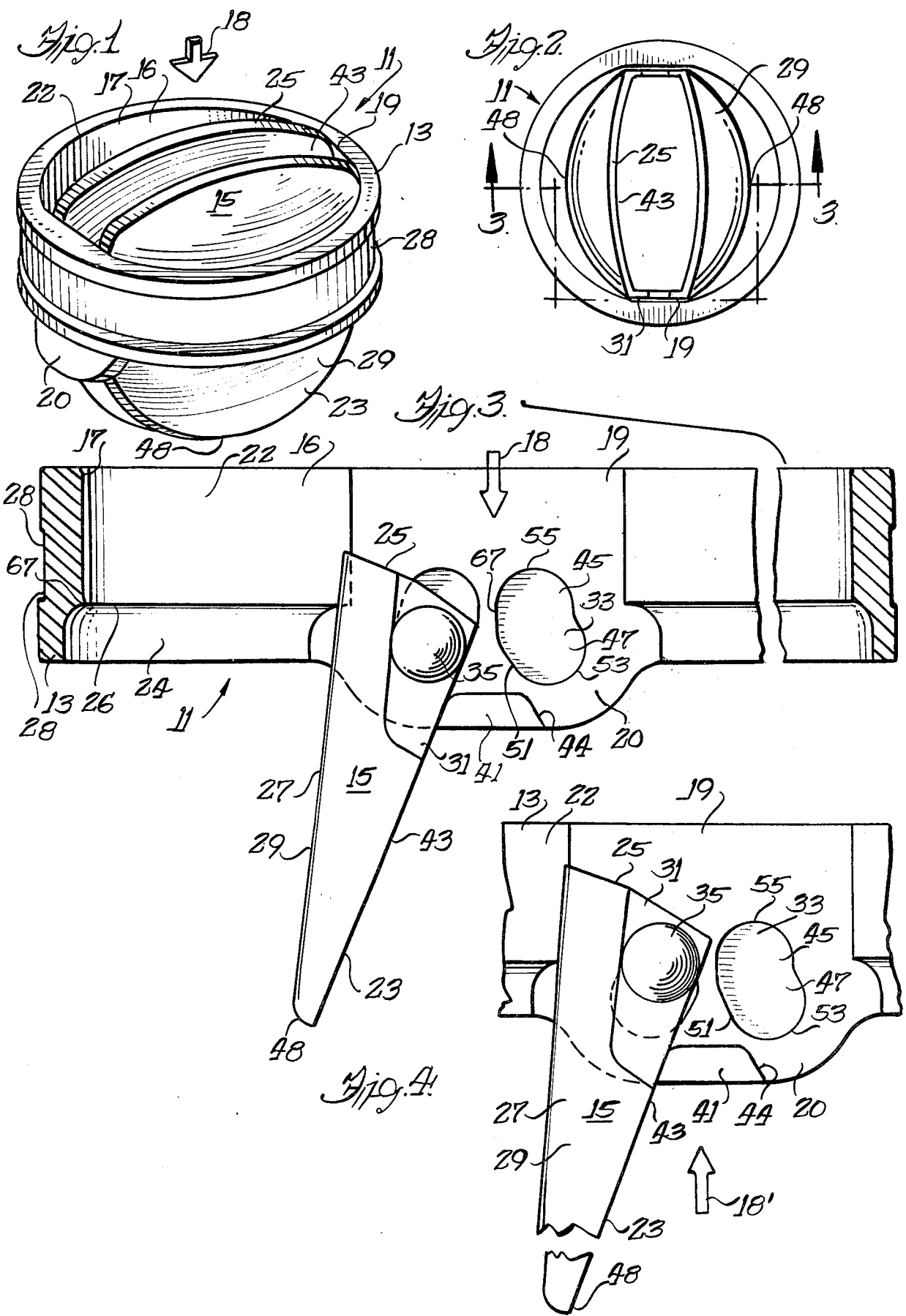

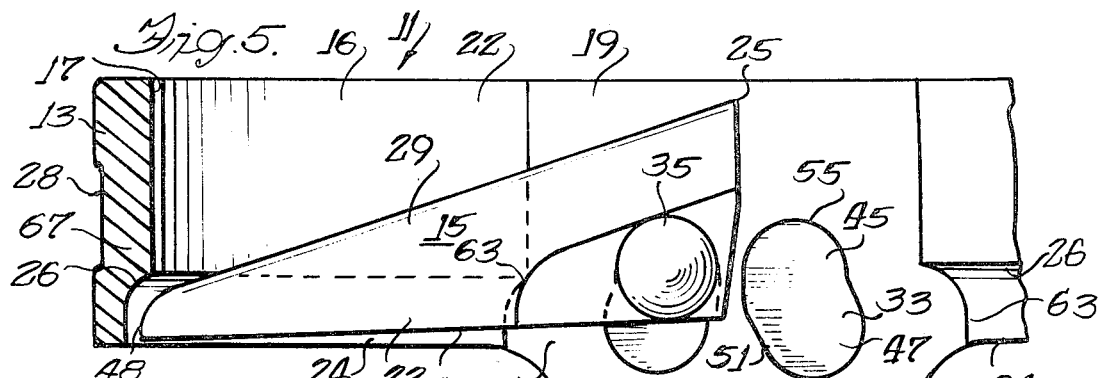
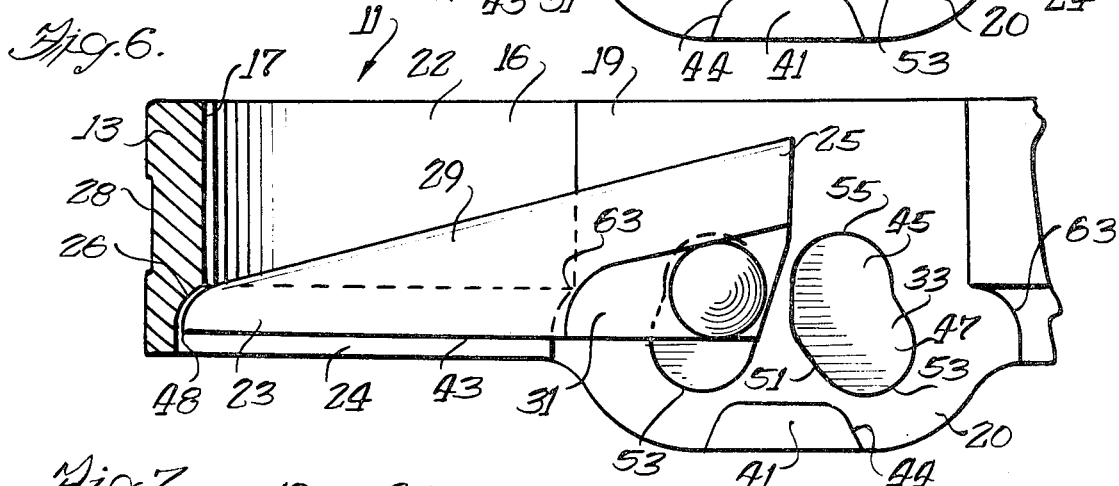
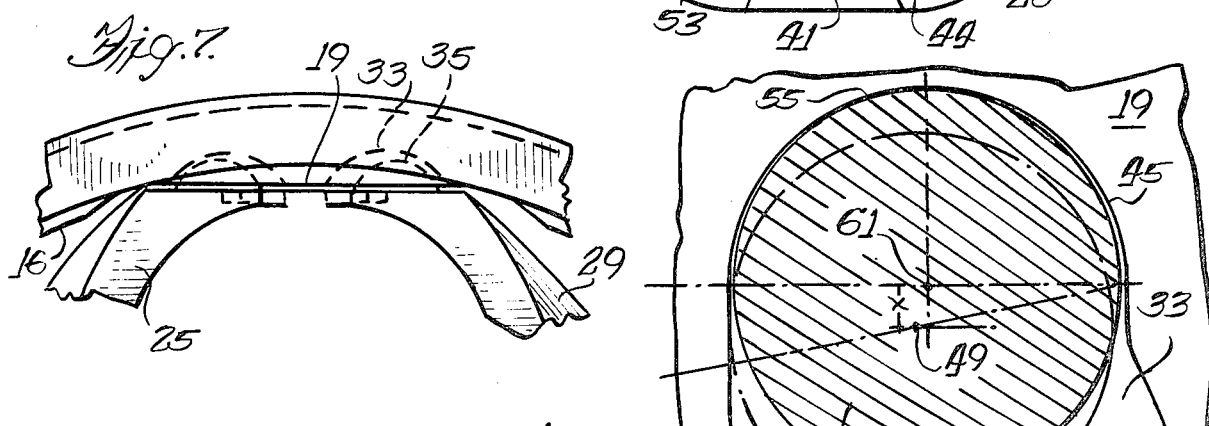
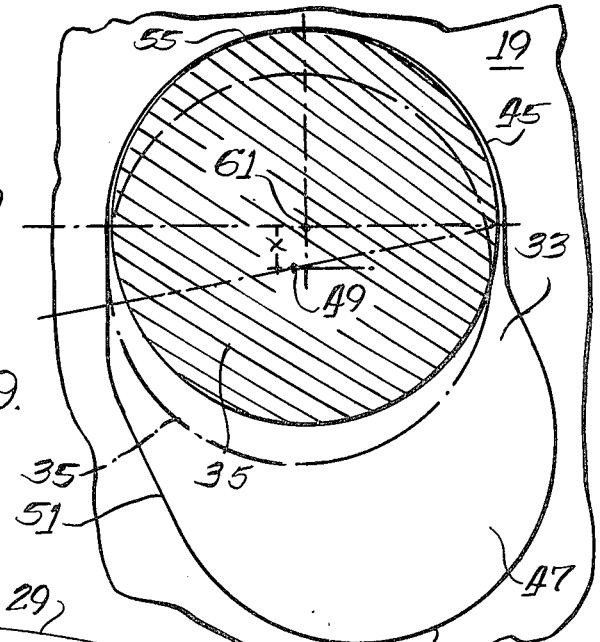
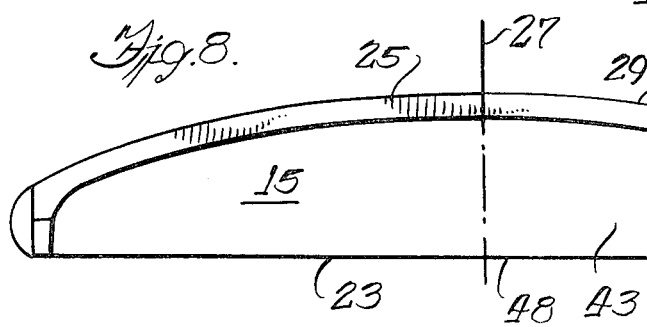

HEART VALVE WITH DOG-LEG PIVOT

This invention relates to heart valve prostheses and more particularly to bileaflet heart valves for implantation into the human body.

BACKGROUND OF THE INVENTION

A large number of heart valve prostheses have been designed for implantation into the human heart valve to replace defective natural heart valves. Although heart valves are merely check valves which open to allow blood flow in a normal or downstream direction and close to prevent regurgitation of blood flowing in a reverse or upstream direction, a good deal of effort has gone into designing and improving the details of heart valves which are designed for implantation in the human body.

In its open position, a valve should provide a passageway which is large and which has good flow characteristics so that blood flows freely therethrough with a minimum of drag and eddy currents. A heart valve should be responsive to blood flow to quickly open in response to blood flow in the normal direction and to close quickly in response to backflow to prevent regurgitation of blood. The heart valve must, of course, be biocompatible and thromboresistant, and in this regard, it is important that all surfaces be well washed by blood to prevent stagnation which might lead to eventual clotting. The opening and closing of the valve should be sufficiently soft so as not to cause hemolysis (breaking of blood cells).

Heart valves, which must withstand countless openings and closings, should be designed to avoid excessive wear, and particular care should be exercised so that the load-bearing surfaces, such as the pivot points and stops, do not wear excessively during the life of the patient. Experience with mechanical heart valves has shown that the major portion of heart valve wear occurs at the moment of closing. The forces during closure are great since both a pressure gradient and substantial fluid momentum (water hammer) act on the valve members at this instant.

SUMMARY OF THE INVENTION

The invention provides a heart valve prosthesis including an annular valve body having elongated depressions formed in its interior wall and a pair of leaflets having guides or projections which interengage with the depressions to guide the leaflets in pivotal and translational movement between closed and open positions. The depressions are dog-leg shaped including upstream sections substantially parallel to the centerline of the valve body and downstream sections which angle outward therefrom. The downstream sections are inclined relative to a centerline plane, and the abutments for determining the open position of the leaflets are arranged in accordance therewith. The arrangement is such that in the open position, when the leaflet guides at the downstream ends of the depressions, the midpoints of the accuate edges of the leaflets are at the point of closest approach so that the midpoints do not come any closer to each other during the first movement of closing when the leaflets initially shift upstream. The upstream sections of the depressions are positioned relative to closed position seats so that, after the projections have initially moved to the upstream ends of the depressions, contact between the leaflets and the seats creates a levering action of the leaflets which results in a slight downstream movement of the projections within the depressions to an intermediate position when the leaflets are fully closed. The force created by backflow blood pressure of the guides against the depressions, which would occur if the leaflet guides seated against the upstream ends of the depressions in the closed position, is thereby unloaded. The dog-leg shape of the depressions, in which the upstream sections and the downstream sections are angled relative to each other, accomplishes both these objectives.

BRIEF DESCRIPTION OF THE DRAWINGS

FIG. 1 is a perspective view of a bileaflet heart valve embodying various features of the invention, shown in its open position;

FIG. 2 is a plan view of the heart valve of FIG. 1;

FIG. 3 is an enlarged view taken generally along line 3—3 of FIG. 2 showing one of the leaflets in elevation and omitting the other;

FIG. 4 is a fragmentary view similar to FIG. 3 showing the one leaflet as it begins to close;

FIG. 5 is a fragmentary view similar to FIG. 3 showing the one leaflet immediately prior to arriving at its closed position;

FIG. 6 is a view similar to FIG. 5 showing the one leaflet in its fully closed position;

FIG. 7 is an enlarged, fragmentary plane view of FIG. 2;

FIG. 8 is an end view of one of the leaflets; and

FIG. 9 is a greatly enlarged fragmentary sectional view through one of the projections, which is shown in its FIG. 5 position in the depression in cross section and in its FIG. 6 position in ghost.

DETAILED DESCRIPTION OF THE PREFERRED EMBODIMENT

Illustrated in FIG. 1 is a heart valve 11 which has an annular valve body or housing 13 which carries a pair of pivoting leaflets or valve members 15 which open and close to control the flow of blood through a central passageway 17 wherein normal flow is downstream in the direction of the arrow 18 (FIG. 3). It should be understood that the heart valve 11 operates in any orientation and is not significantly affected by gravity; however, for ease of explanation, the valve is shown and described with its downstream side facing downward. An interior wall 16 of the valve body 13 defines the passageway 17 which has a generally circular cross section except in the region of a pair of diametrically opposite flat surfaces 19 which divide the remainder of the interior wall into a pair of arcuate portions 22. Enlarged-in-diameter regions 24 at the downstream side of the arcuate portions 22 of the interior wall provide a pair of downstream facing arcuate seats 26 extending between the flat surfaces 19. The flat surfaces 19 extend downstream into a pair of opposite standards 20 which project downstream from the otherwise annular valve body.

The valve body 13 is formed with a peripheral groove 28 about its exterior surface that accommodates a suturing ring (not shown) which may be any of the various types already well known in the art. The suturing ring, of course, facilitates the sewing or suturing of the heart valve 11 to the heart tissue.

The leaflets 15 are proportioned to block blood flow through the valve passageway 17 and have arcuate major edges 23, which abut the arcuate seats 26 in the closed position, and substantially planar minor edges 25, which lie closely adjacent and preferably abut each other in the closed position to positively close the passageway 17. A preferred leaflet configuration, as best seen in FIG. 8, is generally that of a segment of a right elliptical cylindrical tube, with the perpendicular centerline 27 of the leaflet lying along the minor elliptical axis. The tubular leaflets, when disposed within the valve body 13 with their convex surfaces 29 facing upstream, provide an open, generally elliptical central region between the leaflets 15 in the open position, as best seen in FIG. 2, that has little resistance to blood flow. The leaflets may have alternative configurations, such as flat or dome-shaped. Short parallel flat segments 31 on opposite sides at each end of the leaflet centerline 27 span the distances between the major and minor edges 23, 25. The flat segments 31 are spaced apart slightly less than the distance between the opposed flat surfaces 19 of the interior wall and alternately serve as load-bearing surfaces as the leaflets shift laterally during pivoting between the open and closed positions.

The pivotal interconnections between the leaflets 15 and the valve body 13 are provided by a pair of elongated depressions 33 in each of the flat surfaces 19 of the valve body and a pair of opposed guides or projections 35 extending outward from the flat segments 31 at the internal ends of the leaflets 15 and received in the depressions. The configuration of each of the projections 35 is generally that of a sector of a sphere, and the depressions 33 may have arcuate cross sections of slightly greater radius than the radius of the projections so that the projections fit somewhat loosely within the depressions. In any event, the depth of the depressions 33 is greater than the outward extension of the projections 35 so that the flat segments 31 of the leaflets, rather than the projections 35, alternately serve as the load-bearing surfaces thereby alleviating wear on the projections; and accordingly, the radii of curvature may be the same because the regulation of the depth of the projections inherently provides similar clearance in all directions.

The major arcuate edges 23 of the leaflets are proportioned to fit, in the closed position, with their upstream surfaces 29 abutting the seats 26. In the illustrated embodiment, the leaflets have generally semi-circular major edges 23 of a diameter slightly less than the diameter of the enlarged-in-diameter regions 24 of the interior wall and abut the seats 26 in the closed position with their major edges 23 in a plane substantially perpendicular to the passageway centerline.

The open position of the leaflets is determined by a pair of abutments or stops 41 extending radially inward from the downstream ends of the standards 20 to engage the downstream surfaces 43 of the leaflets. The stops 41 preferably have end surfaces 44 which are oriented at desired angles relative to a centerline plane. (Herein centerline plane is the plane through the passageway centerline perpendicular to the opposed flat surfaces 19).

The depressions 33 are elongated to guide the leaflets in translational as well as pivotal motion as the leaflets 15 shift between the open and closed positions. Translational motion has been found to be desirable in heart valves because the continual sliding of the interengaging portions of the valve body and valve members serves to scrape any blood which may begin to accumulate in restricted areas thereby preventing stagnation and subsequent clotting which might impair the function of the valve. Furthermore, the translational movement shifts the leaflets outwardly within the valve body where they allow for a greater central passageway and are less restricting of blood flow through the valve passageway.

The depressions are dog-leg shaped each having an upstream section 45 which is aligned substantially parallel to the centerline plane and a downstream section 47 which angles away from the centerline plane. In the closed position, the leaflets are seated with their projections 35 located at an intermediate location 49 (FIG. 9) which is near the intersection of the upstream section 45 and downstream section 47.

The valve 11 operates as a check valve in response to flowing blood. Flow of blood in the normal or downstream direction pushes and pivots the leaflets 15 to the open position, and backflow of blood exerts a drag on the leaflets which moves them to the closed position. The interengaging projections 35 and depressions 33 are positioned close to the centerline of the valve body 13 so that the greater portion of each leaflet 15 relative to the pivot axis through its projections is distal to the passageway centerline, assuring prompt response in opening and closing.

For a heart valve 11 in the aortic location, as the respective ventricle contracts, the greater amount of force is exerted against the greater distal portion of each leaflet 15 causing the leaflet to swing in the downstream direction with its major edge 23 moving in a wide arc. The elongated depressions 33 provide for translational movement, and as the leaflets, in response to normal blood flow, pivot to the open position, the projections 35 shift to the downstream ends 53 of the depressions.

At the end of the stroke, the respective ventricle relaxes to draw more blood into the chamber from the atrium, and the backflow of blood (in the direction of arrow 18', FIG. 4) from the aorta exerts a drag upon the distal portions of the leaflets 15 which promptly swings each leaflet to its closed position. In order to assure that backflow creates sufficient drag to promptly shift the leaflets to the closed position, it is desirable that the leaflets in their open position be angled somewhat relative to the centerline plane. In the illustrated embodiment, the leaflets are stopped in the open position with the projections 35 at the downstream ends 53 of the depressions and with their downstream surfaces 43 abutting the end surfaces 44 of the stops 41 which angle from the centerline plane between about 10° and about 35°.

The closed position represents the position of maximum separation of the midpoints 48 of the arcuate leaflet edges 23; whereas in the open position, wherein the leaflets abut the stops 41 and the projections 35 are at the downstream ends 53 of the depressions 33, the midpoints 48 of the arcuate edges are at their point of closest approach. Thereafter, the drag created by the reverse blood flow initially shifts the leaflets upstream, as seen in FIG. 4 locating the projections at the extreme upstream ends 55 of the depressions.

The downstream sections 47 of the dog-leg shaped depressions are angled relative to the centerline plane so that, during the initial phase of closing as the projections move upstream within the downstream sections 47, any further leaflet "opening" wherein the midpoints 48 of the arcuate edges would approach each other is substantially eliminated. Stated another way, if the depressions were to instead extend directly upstream, parallel to the passageway centerline, during the initial shifting of the projections upstream from the position shown in FIG. 3, while the downstream leaflet surfaces 43 would slide in continuous contact with the stops 41, there would be a momentary pivoting of the leaflets to positions more closely aligned with the passageway centerline than exists at the fully open position. Such further "opening" of the leaflets in which the midpoints 48 of the arcuate edges momentarily draw slightly closer together would slightly reduce the leaflet-closing drag and would detract from prompt closing of the leaflets because the momentary "opening" movement of the leaflets would have to be first halted and then reversed.

In accordance with the invention, apparent "opening" of the leaflets 15 during the initial phase of closing is substantially eliminated by angling the downstream sections 47 relative to the centerline plane an appropriate amount based upon the location and slope of the stop surfaces 44. The angle is sufficient so that, during the initial upstream translation of the projections, the orientation of the leaflets relative to the stops 41 remains substantially the same, and there is no significant pivoting movement of the midpoints 48 of the arcuate edges 23 toward each other. A slight outward pivoting movement of the midpoints 48 during this initial phase is preferred.

In the illustrated embodiment, the downstream sections 47 angle from the centerline plane at about the same angle as the angled surface 44 of the stops and are there in the same range of between about 10° and about 35°. Adjacent edges 51 of the depressions may be generally colinear with the angled surfaces 44; however, the angle of the stops 44 is preferably slightly larger than that of the downstream sections. During closing, the leaflets 15 initially shift upstream with their projections 35 being guided by the depressions 33 and their downstream surfaces sliding along the angled surfaces 44, and no inward pivoting of the leaflets occurs although some slight outward pivoting is acceptable and can be preferred.

As previously mentioned, the most substantial wear suffered by heart valves occurs when back pressure and backflow are operating upon the leaflets at the final moment of closing. The upstream section 45 of each depression 33 extends slightly upstream of the intermediate location 49 where the projections are located in the fully closed position, and when the arcuate edge region comes in contact with the sealing lip 26, the projection is unloaded during the final moment of closing. During closing the projections 35 initially reach the upstream ends 55 of the depressions 33 centered at point 61, which is a very short distance X (FIG. 9) upstream of the intermediate location, centered at point 49, where they reside in the fully closed position. The distance X preferably less than about 1 mm. and most preferably it is less than 0.5 mm, and in one embodiment, movement of about 0.25 mm has proved effective for guide having a radius of about 1 mm.

Following the initial shifting of the projections 35 to the upstream ends 55 of the depressions 33, the leaflets 15 continue to pivot outward until the upstream surfaces 29 of the leaflets contact the ends 63 of the seats 26 (FIG. 5) creating a levering action in which ends of the seats serve as fulcrums, and which causes the projections 35 to begin to move slightly downstream. As the leaflets 15 move toward complete peripheral contact with the seats 26, the projections are moving away from the upstream ends 55 of the depressions, so that the substantial closing force, as well as the continued backflow pressure of the blood is borne along the extensive interface of the upstream surface 29 of the leaflets 15 and the seats 26. There is substantially no force pressing the projections against the ends of the depressions, and this unloading reduces wear on the projections 35 and depressions 33, promoting long term reliable functioning of the valve.

The dog-leg shape of the depressions 33, having the upstream sections 45 extending generally parallel to the centerline of the passageway 17 and the downstream sections 45 angling outward, takes into consideration the movement of the leaflets during both openings and closing. The upstream vertical sections accommodate movement of the projections 35 during the levering action of the leaflets against the ends 63 of the seats 26 during closing when they move to the intermediate locations 49. As indicated, the edge 63 serves as a fulcrum point, and the projections are translated at the end of a lever arm about the fulcrum. As the projections 35 are levered from the upstream ends 55 of the depressions 33 during closing, they move primarily in a downstream direction. There is some slight displacement inward, i.e., to the left in FIG. 9, as a result of the lever arm action; however, it is accommodated by the tolerance provided between the projections and the depressions. If the depressions 33 were to follow a totally inclined pathway from their upstream ends 53 to their downstream ends 55, such a shape would not allow free movement of the projections as the leaflets pivot against the edge 63, and the projections as the leaflets lever, and the projections would rub against the adjacent edges of the depressions. Although this rubbing should not seriously affect the ability of the leaflets to close, it could result in a significant amount of wear between the projections and the adjacent edges 51 of the depressions. The dimensions of the upstream section accommodate free movement of the projections during leaflet levering, eliminating potential points of substantial wear between the depressions and projections.

The heart valve body 13 may be made of any suitably strong material which is biocompatible and thromboresistant, or can be made so with suitable coatings. The body may be made of graphite, such as that sold under the trademark POCO and thereafter coated with pyrolytic carbon, such as that sold under the trademark PYROLITE. Alternatively, the valve body may be formed as a unitary piece of pyrolytic carbon. The leaflets may be formed entirely of pyrolytic carbon to provide thin responsive leaflets having sufficient strength and wear resistance to withstand countless openings and closings. The leaflets may also be made of coated substrates. The valve body is sufficiently resilient that it can be deformed out of round to provide for insertion of the leaflets; however, it is sufficiently rigid that it will not be deformed by the normal pressures exerted upon it after insertion into the heart.

A typical heart valve according to the present invention, adapted for insertion along with a suturing ring into a heart valve opening of 25 mm, has an outside diameter of about 21.3 mm, an inside diameter of 20.4 mm and enlarged-in-diameter region which provides the seats 20.9 mm in diameter. The valve body is 4.5 mm high, and the upstanding supports project 1.5 mm downstream. The flat surfaces of the interior wall of the valve body are 18.6 mm apart. The leaflet is proportioned to provide about 0.25 mm of clearance between its arcuate edge and the enlarged-in-diameter region in the closed position. The outside surfaces of the flat segments are spaced 18.5 mm apart leaving about 0.05 mm clearance on each side when the leaflets are centered relative to the flat surfaces of the valve body. The guide projections have a radius of 1 mm and extend about 0.62 mm outward of the flat segments of the leaflets while the depressions have a transverse radius of 1 mm and have a maximum depth about 0.68 mm. The angled downstream section of each depression provides for translational movement of the projection of about 0.5 mm between the point of interconnection and the downstream end, and the upstream section also provides for translational movement of the projection of about 0.5 mm, whereas the distance X which the center point of the guide moves between the upstream end and the intermediate location is about 0.26 mm.

Many advantages of the heart valves according to the invention should now be more fully appreciated. The low profile of the heart valves, the large central passageway and the translation of the leaflets outward of the valve body in the open position contribute to excellent blood flow. Almost all surfaces are fully exposed to flowing blood which washes the surfaces and prevents stagnation and clotting, and in particular, the open configuration of the depressions and the spherical shape of the projections leaves no highly restricted areas where stagnation and clotting are likely to begin. Furthermore, the translational movement of the projections within the depressions exposes all surfaces of the depressions to flowing blood, and the sliding of projections along the depressions serves to scrape the surfaces clean during each stroke of the heart. The angled downstream section of the depressions assures that the leaflets will not spread during closing while the upstream sections along with the ends of the seats provide a levering action which unloads the pivots at the crucial moment of closing. The dog-leg shape of the depressions provides a region that accomodates the movement of the projections as the leaflets lever against the ends of the seats.

While the invention has been described in terms of a certain preferred embodiment, modifications obvious to one with ordinary skill in the art may be made without departing from the scope of the invention. For example, the leaflets might seat in their closed position at an acute angle relative to the centerline and in each case, their arcuate major edge would be slightly elliptical to meet the circular valve body. The seating lip need not be continuous and could be replaced by discontinuous lip segments or protuberances including protuberances closely adjacent the flat segments to provide a fulcrum for the levering action of the leaflets.

Various features of the invention are set forth in the following claims.

What is claimed is:

1. A heart valve prosthesis comprising
   an annular valve body having an interior wall forming a central passageway therethrough of generally circular cross section,
   a pair of leaflets proportioned to block blood flow through said passageway when said leaflets are disposed in a closed position,
   each of said leaflets having an arcuate major edge which abuts said valve body in the closed position and a substantially planar minor edge,
   means which pivotably interconnects each of said leaflets and said valve body for relative pivotal movement between the closed position and an open position, which interconnecting means includes pairs of depressions formed in generally opposite locations in said interior wall and pairs of guides extending laterally from each of said leaflets,
   said depressions each having an upstream section which is aligned substantially parallel to the centerline of said central passageway and a downstream section which connects to said upstream section and angles outward from the point of connection, and
   arcuate seat means formed in said heart valve body having surfaces facing downstream with respect to the normal direction of flow of blood through said passageway, said seat means being located relative to upstream ends of said depressions such that, upon the beginning of backflow, said leaflet guides first move from the downstream ends of said downstream sections to the ends of said upstream sections and thereafter finally move downstream within said upstream sections to intermediate locations when said leaflets engage said seat means, so that the force created by backflow blood pressure between said guides and the walls of said depression is unloaded when said leaflets reach said closed position, whereby wear at the location of said interconnecting means is minimized.

2. A heart valve in accordance with claim 1 wherein said arcuate edges are generally semicircular.

3. A heart valve according to claim 1 wherein the major portion of each of said leaflets has a configuration substantially that of a segment of a tube of ellipitical cross section.

4. A heart valve according to claim 3 wherein said leaflets are mounted so that the convex surfaces thereof face upstream.

5. A heart valve according to claim 1 wherein said guides are generally in the shape of sectors of a sphere and said depressions have arcuate cross sections.

6. A heart valve according to claim 1 having abutment means on said valve body to engage the downstream surfaces of said leaflets to stop said leaflets in the open positions.

7. A heart valve according to claim 1 wherein said upstream sections of said depressions are located to allow said projections during closing to move between about 0.25 and about 1 mm upstream of said intermediate locations in said depressions.

8. A heart valve prosthesis according to claim 1 having abutment means on said valve body to engage said leaflets to stop said leaflets in the open position, said downstream sections of said depressions being angled relative to the centerline plane and said abutment means being so located that during the initial translational closing movement of said leaflets, said leaflets are prevented from pivoting inward.

9. A heart valve according to claim 8 wherein a major portion of each of said leaflets has a configuration substantially that of a segment of a tube of elliptical cross section.

10. A heart valve according to claim 9 wherein said leaflets are mounted so that the convex surfaces thereof face upstream.

11. A heart valve according to claim 8 wherein said guides are generally in the shape of sectors of a sphere and said depressions have arcuate cross sections.

12. A heart valve according to claim 8 wherein said downstream sections are inclined toward the centerline plane at angles of between about 10° and about 35°.

13. A heart valve prosthesis comprising
an annular valve body having an interior wall forming a central passageway therethrough of generally circular cross section,
a pair of leaflets proportioned to block blood flow through said passageway when said leaflets are disposed in a closed position,
each of said leaflets having an arcuate major edge which abuts said valve body in the closed position and a substantially planar minor edge,
means which pivotably interconnects each of said leaflets and said valve body for relative pivotal movement between the closed position and an open position, which interconnecting means includes pairs of depressions formed in generally opposite locations in said interior wall and pairs of guides extending laterally from each of said leaflets,
said depressions each having an upstream section which is aligned substantially parallel to the centerline of said central passageway and a downstream section which connects to said upstream section and angles outward from the point of connection, and abutment means on said valve body to engage said leaflets to stop said leaflets in the open position, said downstream sections of said depressions being angled relative to the centerline plane and said abutment means being so located that the initial translational closing movement of said leaflets causes said leaflets to pivot outward.

14. A heart valve according to claim 13 wherein said downstream sections are inclined toward the centerline plane at angles of between about 10° and about 35°.

15. A heart valve in accordance with claim 13 wherein said arcuate edges are generally semicircular.

16. A heart valve according to claim 13 wherein the major portion of each of said leaflets has a configuration substantially that of a segment of a tube of elliptical cross section.

17. A heart valve according to claim 16 wherein said leaflets are mounted so that the convex surfaces thereof face upstream.

18. A heart valve according to claim 13 wherein said guides are generally in the shape of sectors of a sphere and said depressions have arcuate cross sections.

19. A heart valve prosthesis comprising
an annular valve body having an interior wall forming a central passageway therethrough of generally circular cross section,
a pair of leaflets proportioned to block blood flow through said passageway when said leaflets are disposed in a closed position,
each of said leaflets having an arcuate major edge which abuts said valve body in the closed position and a substantially planar minor edge,
means which pivotably interconnects each of said leaflets and said valve body for relative pivotal movement between the closed position and an open position, which interconnecting means includes pairs of depressions formed in generally opposite locations in said interior wall and pairs of guides extending laterally from each of said leaflets, and
abutment means on said annular valve body which engage said leaflets to determine said open position,
said depressions each having a downstream segment which angles toward the centerline of said central passageway in an upstream direction guiding said leaflet in an initial stage of its closing movement in an upstream translational movement while counteracting any tendency of the leaflet to spread apart from the other leaflet and an upstream segment which is aligned substantially parallel to said centerline to permit said guides to move in a direction substantially parallel to said centerline during a later stage of leaflet closing thereby minimizing wear near the end of closing movement.

20. A heart valve according to claim 19 wherein said abutment means are provided at generally diametrically opposite locations and engage downstream-facing surfaces on said leaflets.

21. A heart valve according to claim 19 including levering means positioned relative to the upstream ends of said depressions to act upon said leaflets causing said guides to move slightly downstream during said later stage of closing.

* * * * *

UNITED STATES PATENT AND TRADEMARK OFFICE
CERTIFICATE OF CORRECTION

PATENT NO. : 4,443,894
DATED : April 24, 1984
INVENTOR(S) : Jerome J. Klawitter

It is certified that error appears in the above-identified patent and that said Letters Patent is hereby corrected as shown below:

Column 1, line 59, change "when" to --with--.

Column 7, line 46, change "each" to --such--.

Signed and Sealed this

Twentieth Day of November 1984

[SEAL]

Attest:

GERALD J. MOSSINGHOFF

Attesting Officer          Commissioner of Patents and Trademarks